United States Patent [19]
Lui et al.

[11] Patent Number: 5,969,197
[45] Date of Patent: *Oct. 19, 1999

[54] PROCESS FOR THE PREPARATION OF CHLORO-FLUORO-BUTENES

[75] Inventors: Norbert Lui, Cologne; Albrecht Marhold, Leverkusen; Dietmar Bielefeldt, Ratingen, all of Germany

[73] Assignee: Bayer Aktiengesellschaft, Leverkusen, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/257,237

[22] Filed: Jun. 9, 1994

Related U.S. Application Data

[63] Continuation of application No. 08/041,732, Apr. 1, 1993, abandoned.

[30] Foreign Application Priority Data

Apr. 10, 1992 [DE] Germany .................. 42 12 084

[51] Int. Cl.$^6$ ..................................... C07C 17/20
[52] U.S. Cl. ............................................. 570/160
[58] Field of Search ............................... 570/160

[56] References Cited

U.S. PATENT DOCUMENTS 3,149,170  9/1964  Clark et al.

*Primary Examiner*—Alan Siegel
*Attorney, Agent, or Firm*—Sprung Kramer Schaefer & Briscoe

[57] ABSTRACT

Avoiding hexachlorobutadiene as the starting material, 2-chloro- and 2,3-dichloro-1,1,1,4,4,4-hexafluoro-2-butene are prepared by reacting a chlorobutene derivative of the formula (I)

$$Cl_2C=CH-X \quad (I)$$

in which

X represents $CCl=CCl_2$ or $CCl_2-CCl_2H$ with hydrogen fluoride and chlorine in the presence of a catalyst at temperatures in the range of 50 to 550° C.

5 Claims, No Drawings

PROCESS FOR THE PREPARATION OF CHLORO-FLUORO-BUTENES

This application is a continuation, of application Ser. No. 08/041,732, filed Apr. 1, 1993 now abandoned.

The present invention relates to a process for the simultaneous preparation of 2-chloro- and 2,3-dichloro-1,1,1,4,4, 4-hexafluoro-2-butene from chlorobutene derivatives.

2-Chloro-1,1,1,4,4,4-hexafluoro-2-butene is a known intermediate for the preparation of sodium trifluoroacetate. Known preparation methods are the reaction of hexachlorobutadiene with hydrogen fluoride and chlorine with the addition of antimony pentachloride and C.A. 46, 7987 i to 7988 a) and the reaction of hexachlorobutadiene with hydrogen fluoride with the addition of catalytic amounts of titanium tetrahalide, antimony trihalide and/or antimony pentachloride (German Offenlegungsschrift 37 25 213).

2,3-Dichloro-1,1,1,4,4,4-hexafluoro-2-butene is a known intermediate for the preparation of hexafluorobutane, a heat transfer agent, and of trifluoroacetic acid. It can be prepared from hexachlorobutadiene by reaction with hydrogen fluoride and chlorine with the addition of antimony pentachloride and C.A. 46, 7987 i to 7988 a).

The hexachlorobutadiene required as the starting material for these processes is nowadays no longer produced on an industrial scale, as it has come under suspicion of being carcinogenic. A process is therefore needed for the preparation of 2-chloro- and 2,3-dichloro-1,1,1,4,4, 4-hexafluoro-2-butene, which employs starting materials that can be prepared on an industrial scale.

We have now found a process for the simultaneous preparation of 2-chloro- and 2,3-dichloro-1,1,1,4,4,4-hexafluoro-2-butene, characterised in that a chlorobutene derivative of the formula (I)

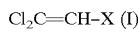

$$Cl_2C=CH-X \quad (I)$$

in which

X represents $CCl=CCl_2$ or $CCl_2-CCl_2H$ is reacted with hydrogen fluoride and chlorine in the presence of a catalyst at temperatures in the range of 50 to 550° C.

The starting compounds of the formula (I) required for this process can be obtained, for example, according to Zh. Org. Khim. 17(2), 272 to 275.

The other starting materials required, hydrogen fluoride and chlorine, are preferably employed in anhydrous form and as such are commercially available.

The hydrogen fluoride, for example, can be employed in amounts from 5 to 100 mol, based on 1 mol of a chlorobutene derivative of the formula (I). This amount is preferably from 10 to 50 mol per mol of chlorobutene derivative of the formula (I).

The chlorine, for example, can be employed in amounts from 1 to 3 mol, based on 1 mol of chlorobutene derivative of the formula (I). This amount is preferably from 1.1 to 2.2 mol per mol of chlorobutene derivative of the formula (I).

The process according to the invention can be carried out in the liquid phase and in the gas phase. When working in the liquid phase, i.e. at correspondingly low temperatures and/or at elevated pressure, the usual catalysts for chlorine/fluorine exchange reactions in the liquid phase can be employed, for example titanium halogenides, in particular titanium tetrachloride, niobium halogenides, in particular niobium pentachloride, tantalum halogenides, in particular tantalum pentachloride, antimony trifluoride, antimony pentafluoride, antimony pentachloride and/or mixed antimony pentahalides, for example those of the empirical formula $SbCl_nF_{5-n}$ with n=0.1 to 4.9. Such catalyst can be employed individually or in any mixture with each other. If required, fluorosulphonic acid can be employed as a cocatalyst.

If the process according to the invention is carried out in the gas phase, i.e. at correspondingly high temperatures and low pressures, the usual catalysts for chlorine/fluorine exchange reactions in the gas phase can be used. Possible choices are, for example, halides and oxides of metals and transition metals. Particularly suitable are chlorides, fluorides and/or oxides of copper chromium, iron, bismuth, zinc, lanthanum, cerium, zirconium, vanadium, molybdenum, tungsten and/or nickel, which oxides can optionally be mixed. Preferred are chromium(III) salts on their own, or in a mixture with chlorides of the other metals mentioned and/or their fluorides and/or their oxides. In the gas phase process, the catalysts can be employed as such, e.g. in the form of pellets, or applied to a support, for example on alumina, magnesium oxide, magnesium fluoride, calcium fluoride, zinc chloride and/or activated carbon.

The amount in which catalysts are used in the process according to the invention is not critical. For economic reasons, the amount of catalyst is advantageously chosen so as to achieve at least 60% conversion. When working in the gas phase, for example, 50 g to 5 kg of the chloro-butene derivative of the formula (I) can be passed over a liter of the catalyst per hour. When working in the liquid phase it is possible, for example, to use 0.1 to 30% by weight of catalyst, based on the chloro-butene derivative employed of the formula (I).

If the process is to be carried out in the liquid phase, it is always necessary to work in sealed vessels or under pressure, because hydrogen fluoride boils at around 20° C. at atmospheric pressure. Reaction conditions suitable for working in the liquid phase are, for example, temperatures from 50 to 200° C. and pressures from 6 to 50 bar.

If the process according to the invention is carried out in the gas phase, the temperature may, for example, be in the range from 200 to 550° C. Reaction conditions preferred for the gas phase are temperatures from 250 to 480° C. and pressures in the range from 0.5 to 3 bar.

If the process according to the invention is carried out batchwise, in particular in the liquid phase, it is generally advantageous, after the reaction has ended, to continue stirring for some time at the final temperature, for example for 1 to 5 hours. If the process according to the invention is carried out continuously, in particular in the gas phase, it is generally advantageous to maintain the gas stream, after it has passed the catalyst, at the reaction temperature for a little longer, for example for 5 to 30 minutes.

The reaction mixture present after the reaction has ended can, after cooling down and condensation if required, be worked up by, for example, first removing any hydrogen fluoride still present, e.g. by phase separation or by distillation, and by subjecting the residue to fractional distillation or by mixing the residue freed of hydrogen fluoride with ice, separating the organic phase formed and subjecting said phase to fractional distillation. If catalysts soluble in the reaction mixture have been used, these may be recovered if appropriate, for example by extracting the reaction mixture after the removal of the hydrogen fluoride with a tartaric acid solution.

Compared to the known processes for the preparation of 2-chloro-and2,3-dichloro-1,1,1,4,4,4-hexafluoro-2-butene, the present invention has the advantage of using as a starting material not the no longer industrially available hexachlorobutadiene, but chlorobutene derivatives of the formula (I) which can be prepared readily and in large quantities from trichloroethylene.

It was impossible to foresee that the reaction of chlorobutene derivatives of the formula (I) with hydrogen fluoride and chlorine would give such good results both in the liquid phase and in the gas phase, since, in contrast to the situation when hexachlorobutadiene is used, side reactions and fission reactions had to be expected.

EXAMPLE 1

110.4 g of $BiCl_3$ were dissolved in 150 g of 18% by weight aqueous hydrochloric acid, and this solution was then mixed with a solution of 16.76 g of $FeCl_3 \times 6\ H_2O$ in 30 g of water. A kneader was charged with 250 g of MgO, and the solution of the metal salts was added. During kneading, a further 170 ml of water were added. After kneading for 1.5 hours, the kneaded mass was dried, ground and, after adding 2% by weight of graphite, was prilled. The atomic ratio Mg:Bi:Fe was 1:0.06:0.04.

An externally electrically heatable nickel tube having an internal diameter of 30 mm was filled with 350 ml of the catalyst thus prepared, and 5 mol of hydrogen fluoride were passed through at 350° C. in the course of 3 hours. The gas used was a mixture of hydrogen fluoride with nitrogen in a molar ratio of 1:2.

Subsequently, 80 g of hexachlorobutene (formula (I), $X=CCl_2-CCl_2H$), 28 g of chlorine and 400 ml of hydrogen fluoride (measured as liquid) per hour were passed over the catalyst at 460° C. The gases leaving the reaction tube were cooled down and condensed in a receiver cooled to −50° C. After operating for 2 hours, the supply of hexachlorobutene, chlorine and hydrogen fluoride was turned off, and after a further 30 minutes the contents of the receiver were subjected to phase separation. The bottom, organic phase was poured onto 200 g of ice and after warming to 10° C. was again separated from the aqueous phase. 112 g of reaction product were obtained which contained 18.5% by weight of 2-chloro-1 11,1,4,4, 4-hexafluoro-2-butene (cis/trans) and 57.5% by weight of 2,2-dichloro-1,1,1,4,4,4-hexafluoro-2-butene.

EXAMPLE 2

1145 ml of water and 588 g of 28% by weight aqueous ammonia were placed in a flask which was fitted with a mechanical stirrer and a dropping funnel. By means of the dropping funnel, 520 g of a 37% by weight aqueous solution of chromium(III) chloride and 1 liter of water were added in the course of an hour. The resulting precipitate was separated, washed with water and placed in a vacuum oven at 70° C. The resulting, still moist paste containing hydrated chromium(III) oxide was cut into small cubes and then dried at 480° C. in a nitrogen atmosphere.

350 ml of this catalyst were pretreated with hydrogen fluoride as described in Example 1, followed by the admission, as described in Example 1, of 80 g of hexachlorobutene, 30 g of chlorine and 220 g of hydrogen fluoride. 106 g of a reaction product were obtained which contained 12.7% by weight of 2-chloro-1,1,1,4,4, 4-hexafluoro-2-butene and 61.3% by weight of 2, 3-dichloro-1,1,1,4,4,4-hexafluoro-2-butene.

EXAMPLE 3

$CrCl_3 \times 6\ H_2O$ was dissolved in water. Magnesium oxide and graphite were added to this solution, and the resulting paste-like mass was kneaded. The paste-like reaction product obtained was broken into cubes with edges 0.5 cm in length and then dried for 16 hours at 100° C. The finished catalyst contained 17% by weight of $CrCl_3$, 76% by weight of MgO and 7% by weight of graphite.

This catalyst was treated with hydrogen fluoride as described in Example 1, followed by the admission, as described in Example 1, of 80 g of hexachlorobutene, 28 g of chlorine and 400 ml of hydrogen fluoride per hour.

117.5 g of a reaction product were obtained which contained 11.6% by weight of 2-chloro-1,1,1,4,4, 4-hexafluoro-2-butene and 66.1% by weight of 2, 3-dichloro-1,1,1,4,4,4-hexafluoro-2-butene.

EXAMPLE 4

300 g of $CrCl_3 \times 6\ H_2O$ and 30 g of $MgF_2$ in 10 l of water were heated to 90° C. After 1 hour, 1300 g of 11% by weight aqueous ammonia were metered in. The mixture was then stirred for 1 more hour and then left to cool, and the precipitated solid was filtered off by means of a filter nutsche. The solid was twice washed with water, dried, powdered, and homogeneously mixed with 2% by weight of graphite. This mixture was pressed into tablets having a size of 4 mm.

The catalyst thus obtained was pretreated with hydrogen fluoride as described in Example 1, followed by the admission, as described in Example 1, of 80 g of pentachlorobutadiene, 27 g of chlorine and 230 g of hydrogen fluoride per hour. 98 g of a reaction product were obtained which contained 19.2% by weight of 2-chloro-1, 1,1,4,4,4-hexafluoro-2-butene and 53.4% by weight of 2,3-dichloro-1,1,1,4,4,4-hexafluoro-2-butene.

EXAMPLE 5

400 g of hexachlorobutene, with the addition of 2 ml of antimony pentachloride, were chlorinated using 1.7 mol of chlorine at 40° C. The mixture was then placed in an autoclave. There, 600 ml of anhydrous hydrogen fluoride and a further 50 g of antimony pentachloride were added. The reaction mixture, under autogenous pressure, was heated to 140° C. for 5 hours, the resulting hydrogen chloride being vented in such a way that the hydrogen fluoride remained in the liquid phase. After cooling down to room temperature, the mixture was poured onto ice, and the organic phase was separated. 240 g of reaction product were obtained which contained 20% by weight of 2-chloro-1,1, 1,4,4,4-hexafluorobutene. The less highly fluorinated fractions can be recycled as starting material for the fluorination.

What is claimed is:

1. A process for the simultaneous preparation of 2-chloro- and 2,3-dichloro-1,1,1,4,4, 4-hexafluoro-2-butene, whereby the amount of said 2, 3-dichloro-1,1,1,4,4,4-hexafluoro-2-butene produced is greater than the amount of said 2-chloro-1,1,1,4,4,4-hexafluoro-2-butene produced, which comprises reacting a chlorobutene derivative of the formula (I)

in which

X represents $CCl=CCl_2$ or $CCl_2-CCl_2-CCl_2H$ with hydrogen fluoride and chlorine in the presence of a catalyst at a temperature in the range of 50 to 550° C.

2. The process of claim 1, which comprises carrying it out in the gas phase at from 200 to 550° C. and in the presence of a catalyst which is selected from the group consisting of halides and oxides of metals and transition metals.

3. The process of claim 1 which comprises carrying it out in the liquid phase at from 50 to 200° C. from 6 to 50 bar, and in the presence of a catalyst selected from the group consisting of titanium halogenide, niobium halogenide, tantalum halogenide, antimony trifluoride, antimony pentafluoride, antimony pentachloride and mixed antimony pentahalides.

4. The process of claim 1, which comprises that 5 to 100 mol of hydrogen fluoride and 1 to 3 mol of chlorine are used, each based on 1 mol of chlorobutene derivative of the formula (I).

5. The process of claim 1, which comprises carrying out in the gas phase and employing catalysts containing chromium(III) salts.

* * * * *